United States Patent [19]
Ho et al.

[11] Patent Number: 5,594,134
[45] Date of Patent: Jan. 14, 1997

[54] PROCESS OF SYNTHESIZING N-ACYL AUXILIARIES

[75] Inventors: Guo-Jie Ho, Rahway; David J. Mathre, Skillman, both of N.J.

[73] Assignee: Merck & Co., Inc., Rahway, N.J.

[21] Appl. No.: 414,541

[22] Filed: Mar. 31, 1995

[51] Int. Cl.$^6$ .................. C07D 205/04; C07D 207/12
[52] U.S. Cl. ............... 540/362; 540/451; 540/529; 546/193; 546/208; 546/243; 548/540
[58] Field of Search .................. 540/362, 451, 540/529; 546/193, 208, 243; 548/540

[56] References Cited

U.S. PATENT DOCUMENTS 5,461,162  10/1995  Ho et al. .................. 548/188

OTHER PUBLICATIONS

J. of Org. Chem., vol. 54, No. 3, Feb. 3, 1989, pp. 513–515, by S. Kano, et al.
Tetrahedron vol. 49, No. 9, pp. 1841–1852 (1993), by T. Ishizuka, et al.
Helvetica Hemica Acta, vol. 74 (1991) pp. 617–627, by A. Thaler, et al.
J. Org. Chem. 1991, 56, pp. 112–119, by Y. Yamamoto, et al.
J. Chem. Soc., Chem. Commun., 1992 pp. 1673–1674, by A. Ghosh, et al.
J. Org. Chem., vol. 55, No. 15 (1990) pp. 4585–4595, by D. Curran, et al.
J. Am. Chem. Soc., vol. 112, No. 7 (1990), pp. 2767–2772, by W. Oppolzer, et al.
J. Am. Chem. Soc. vol. 110, No. 25 (1988), pp. 8477–8482, by F. Davis, et al.
Liebigs Ann. Chem. (1989) pp. 739–750, by P. Binger, et al.
J. Am. Chem. Soc. (1982), 104, pp. 1737–1739, by E. Evans, et al.
Pure & Appl. Chem., vol. 62, No. 7, pp. 1241–1250 (1990), by W. Oppolzer.
J. Am. Chem. Soc., vol. 103, No. 8 (1981), pp. 2127–2129, by D. Evans, et al.
J. Am. Chem. Soc., vol. 106, No. 4 (1984), pp. 1154–1156, by D. Evans, et al.
Synthesis, Jun. 1992, pp. 582–586, by C. Thom, et al.
Synthesis in the Quinolizidine Series, Mar. 1949, vol. 71, pp. 879–886, by V. Boekelheide, et al.
Helvetica Chimica Acta, vol. 67 (1984), pp. 1397–1401, by W. Oppolzer, et al.
Helvetica Chimica Acta, vol. 70 (1987) pp. 1666–1675, by W. Oppolzer, et al.
Tetrahedron, vol. 43, No. 9 (1987), pp. 1969–2004, by W. Oppolzer.

*Primary Examiner*—Joseph K. McKane
*Attorney, Agent, or Firm*—Richard C. Billups; Mark R. Daniel

[57] ABSTRACT

A process of synthesizing N-acyl auxiliary compounds is disclosed. A compound of the formula:

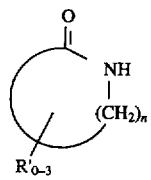

B is reacted with an anhydride in the presence of a lithium salt and an amine base to produce the N-acylated auxiliary.

4 Claims, No Drawings

5,594,134

PROCESS OF SYNTHESIZING N-ACYL AUXILIARIES

BACKGROUND OF THE INVENTION

Chiral auxiliaries have been extensively used in asymmetric syntheses. Traditionally, N-acyl 2-oxazolidinones have been synthesized by lithiating the oxazolidinone with n-butyl lithium at −78° C., followed by acylating with an acyl chloride. N-acyl sultams have similarly been synthesized by deprotonation with NaH, followed by N-acylation with an acyl chloride. Such two step procedures have been used to convert the oxazolidinone or sultam to the respective trimethylsilyl derivatives, followed by reaction with excess acyl chloride in refluxing toluene. Neither of these synthesis schemes is particularly useful when the acyl side chain contains substituent groups that are reactive. Also, these reactions take an inordinately long time to run to completion. The present invention overcomes the disadvantages in these processes.

When deprotonation is effected with a strong base, followed by acylation using an acid chloride or anhydride, side reactions frequently occur if the substrate contains other functional groups.

Copending application Ser. No. 281,394, filed on Jul. 27, 1994 addresses the N-acylation of oxazolidinones and 2,10-sultams. The present application addresses the N-acylation of other ring systems.

SUMMARY OF THE INVENTION

A process of synthesizing an N-acyl auxiliary compound of the formula:

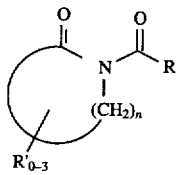

(A)

is disclosed.

R and R' independently represent members selected from the group consisting of:

(a) —$C_{1-6}$ alkyl, —$C_{2-6}$ alkenyl or —$C_{2-6}$ alkynyl;
(b) —$C_{1-6}$ alkyl, —$C_{2-6}$ alkenyl or —$C_{2-6}$ alkynyl substituted with from 1–3 groups selected from: —$NH_2$; —OH; —COOH, —COO($C_{1-4}$) alkyl, —$OC_{1-4}$ alkyl; —C(O)—$C_{1-4}$ alkyl; —OC(O)$C_{1-4}$ alkyl; —NH($C_{1-6}$ alkyl); —NH($C_{2-6}$ alkenyl); —NH($C_{2-6}$ alkynyl); —N($C_{1-6}$ alkyl)$_2$; —N($C_{2-6}$ alkenyl)$_2$; —N($C_{2-6}$ alkynyl)$_2$; —OC(O)$NH_2$; —OC(O)NH$C_{1-4}$ alkyl; —OC(O)N($C_{1-4}$ alkyl)$_2$; -aryl; -heteroaryl; —$C_{3-8}$ cycloalkyl; -heterocyclyl; -halo; —NHC(O)O$C_{1-6}$ alkyl; —N($C_{1-4}$ alkyl)C(O)O$C_{1-6}$ alkyl, and -aryl, heteroaryl, $C_{3-8}$ cycloalkyl or heterocyclyl substituted with from 1–3 groups selected from halo, hydroxy, —$C_{1-4}$ alkyl, —$C_{1-4}$ alkoxy, hydroxy-$C_{1-4}$ alkyl, -amino, —NH($C_{1-4}$ alkyl) and —N($C_{1-4}$ alkyl)$_2$;

(c) aryl, heteroaryl, $C_{3-8}$ cycloalkyl or heterocyclyl, unsubstituted or substituted with from 1–3 groups selected from halo, hydroxy, $C_{1-4}$ alkoxy, hydroxy-$C_{1-4}$ alkyl, amino, $C_{1-4}$ alkylamino, and di-$C_{1-4}$ alkylamino;

(d) $C_{1-6}$ alkyl, $C_{2-6}$ alkenyl or $C_{2-6}$ alkynyl substituted with (1) 1 to 3 groups selected from: —NHP; —$NP_2$; —OP; —$CO_2P$; —NP($C_{1-6}$ alkyl); —NP($C_{2-6}$ alkenyl); —NP($C_{2-6}$ alkynyl); —OC(O)NHP; —OC(O)$NP_2$; OC(O)NP($C_{1-6}$ alkyl); —NPC(O)O($C_{1-6}$ alkyl); aryl, heteroaryl, $C_{3-8}$ cycloalkyl or heterocyclyl substituted with from 1–3 groups selected from —OP, —$C_{1-3}$ alkyl-OP, —NHP, —$NP_2$, —$C_{1-3}$ alkyl-NHP, —$C_{1-3}$ alkyl-$NP_2$, —NP—$C_{1-3}$ alkyl, and 0–3 members selected from the group consisting of: halo, $C_{1-3}$ alkyl, $C_{1-3}$ alkoxy, and —N($C_{1-3}$ alkyl)$_2$;

and (2) 0 to 3 groups selected from the group consisting of: —COO($C_{1-3}$) alkyl, —O$C_{1-4}$ alkyl; —C(O)—$C_{1-4}$ alkyl; —N($C_{1-6}$ alkyl)$_2$; —N($C_{2-6}$ alkenyl)$_2$; —N($C_{2-6}$ alkynyl)$_2$; —OC(O)N($C_{1-4}$ alkyl)$_2$; aryl; heteroaryl; $C_{3-8}$ cycloalkyl; heterocyclyl; halo; —N($C_{1-3}$ alkyl)C(O)O$C_{1-6}$ alkyl; and aryl, heteroaryl, —$C_{3-8}$ cycloalkyl or heterocyclyl substituted with from 1–3 groups selected from: halo, —$C_{1-3}$ alkyl, —$C_{1-3}$ alkoxy and —N($C_{1-3}$ alkyl)$_2$, and (e) aryl, heteroaryl, $C_{3-8}$ cycloalkyl or heterocyclyl substituted with:

(1) from 1 to 3 members selected from the group consisting of: —OP, —$C_{1-4}$ alkyl-OP, —NHP, —$NP_2$, —$C_{1-4}$ alkyl-NHP, —$C_{1-4}$ alkyl-$NP_2$ and —NP$C_{1-4}$ alkyl,
and
(2) from 0 to 3 members selected from the group consisting of: halo, —$C_{1-4}$ alkoxy and —N($C_{1-4}$ alkyl)$_2$;
wherein P represents a protecting group, and n represents an integer of from 2 through 7.

A compound of the formula:

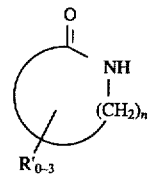

(B)

wherein R' and n are as defined above, is reacted with an anhydride represented by the formula:

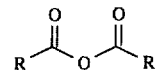

(C)

wherein each R is the same or different, and is as previously defined, in the presence of a lithium salt and an amine base to produce:

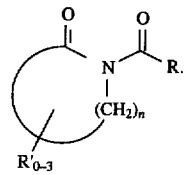

(A)

DETAILED DESCRIPTION OF THE INVENTION

As used herein, the following terms and definitions apply unless otherwise indicated.

The term "alkyl" refers to a monovalent alkane (hydrocarbon) derived radical containing from 1 to 6 carbon atoms unless otherwise defined. It may be straight or branched. Preferred alkyl groups include methyl, ethyl, propyl, isopropyl, butyl and t-butyl. When substituted, alkyl groups may be substituted with up to four substituent groups, at any available point of attachment. When the alkyl group is said to be substituted with an alkyl group, this is used interchangeably with "branched alkyl group".

Alkylidene refers to a divalent group —(CH$_2$)$_{2-5}$—. When the alkylidene is substituted, the substituent groups can be at any available point of attachment. All stereoconfigurations at asymmetric carbon atoms are included in the invention.

The term "alkoxy" refers to a C$_{1-4}$ alkoxy radical: —OC$_{1-4}$ alkyl. The preferred alkoxy group is methoxy.

Cycloalkyl is a specie of alkyl, containing from 3 to 15 carbon atoms, preferably 3–8 carbon atoms, without alternating or resonating double bonds between carbon atoms. It may contain from 1 to 4 rings which are fused. The preferred cycloalkyl groups are cyclopentyl and cyclohexyl.

When a bond is indicated by a wavy line, this means that the stereoconfiguration is contemplated. For example,

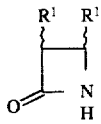

includes the following configurations:

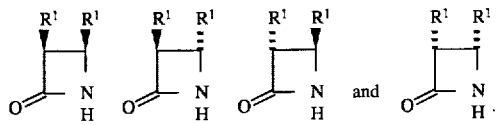

Such compounds can be used in pure form or in combination as a mixture of isomers.

The term "alkenyl" refers to a hydrocarbon radical straight, branched or cyclic containing from 2 to 6 carbon atoms and at least one carbon to carbon double bond. Preferred alkenyl groups include ethenyl, propenyl, butenyl and cyclohexenyl.

The term "alkynyl" refers to a hydrocarbon radical straight or branched, containing from 2 to 6 carbon atoms and at least one carbon to carbon triple bond. Preferred alkynyl groups include ethynyl, propynyl and butynyl.

Aryl refers to aromatic rings e.g., phenyl, substituted phenyl and like groups, as well as tings which are fused, e.g., naphthyl, phenanthrenyl and the like. An aryl group thus contains at least one ring having at least 6 atoms, with up to five such tings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "heteroatom" means O, S or N selected on an independent basis.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms are optionally replaced by a heteroatom selected from O or S, and in which from 1 to 3 additional carbon atoms are optionally replaced by nitrogen atoms, said heteroaryl group being optionally substituted as described herein.

Heteroaryl thus includes aromatic and partially aromatic groups which contain one or more heteroatoms. Examples of this type are pyrrole, pyridine, oxazole, thiazole and oxazine. Additional nitrogen atoms may be present together with the first nitrogen and oxygen or sulfur, giving, e.g., thiadiazole. Preferred heteroaryl groups are thiazolyl, imidazolyl, pyridyl and pyrrolyl.

The term "heterocycloalkyl" refers to a cycloalkyl group (nonaromatic) in which one of the carbon atoms in the ring is replaced by a heteroatom, and in which up to three additional carbon atoms may be replaced by heteroatoms. Preferred heterocycloalkyl groups include piperidinyl, pyrrolidinyl and tetrahydrofuranyl.

Halogen and "halo" refer to bromine, chlorine, fluorine and iodine.

The term "lithium salt" is used in the conventional sense, and refers to substantially non-basic lithium salts. The following lithium salts are representative: lithium bromide, lithium chloride, lithium fluoride, lithium iodide, lithium perchlorate, lithium nitrate, lithium sulfate and lithium tetrafluoroborate. Preferred salts are lithium chloride and lithium bromide.

Amine bases as used herein refers to triethylamine, pyridine, diisopropylethylamine, lutidine, 1,8-diazobicyclo[5.4.0]undec-7-ene and 1,5-diazabicyclo[4.3.0]non-5-ene.

The R and R' groups in many instances are in protected form. When a functional group is termed "protected", this means that the group is in modified form to preclude undesired side reactions at the protected site. All such variations are included in the presently claimed invention. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification. While the protecting groups are generally designated by the variable P, different protecting groups are preferable for different functionalities.

Where hydroxyl is shown in protected form as —OP, this can also be designated —OP$^1$. When a protecting group is present attached to a nitrogen atom, as in —NHP, —NP$_2$ and the like, these protecting groups can be designated interchangeably as P$^2$. Lastly, when a protecting group is present on a carboxyl group, as in —COOP, such protecting groups can also be designated interchangeably as P$^3$.

Examples of suitable hydroxyl protecting groups (P$^1$) which can be used in the syntheses described herein include the following: t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Preferred hydroxyl protecting groups P$^1$ are trimethylsilyl and triethylsilyl.

Examples of suitable amino protecting groups (P$^2$) include the following: t-butoxycarbonyl (t-BOC), 2,2,2-trichloroethoxycarbonyl, allyloxycarbonyl, benzyloxycarbonyl, o- and p-nitrobenzyloxycarbonyl. The preferred amino protecting group (P$^2$) is t-BOC.

Examples of suitable carboxyl protecting groups (P$^3$) include the following: benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl. A preferred carboxyl protecting group (P$^3$) is p-nitrobenzyl.

The structure

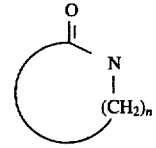

contains an amide linkage, the nitrogen atom of which is reacted with the anhydride to form an imide in accordance with the process described herein. In this structure, n represents an integer from 2 to 7. The rings thus can be as follows:

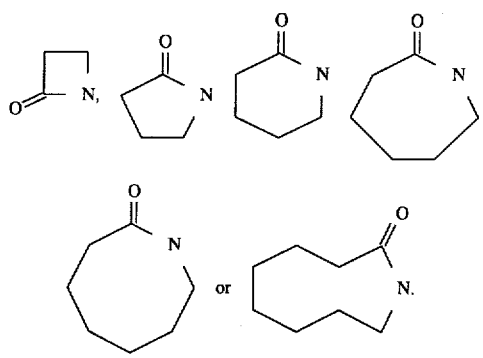

The preferred values of n are 2, 3 and 4.

In one preferred embodiment of the invention, the lactam is reacted with a mixed anhydride as described below in the presence of a lithium salt and an amine base. The mixed anhydride has the formula $R^1$—C(O)—O—(O)—$R^2$. $R^1$ and $R^2$ are different from each other and are selected from the values of R. Lithium salts which can be used in this particular embodiment include the halide salts, e.g., LiCl and LiBr.

Amine bases which are suitable for use herein include triethylamine ($Et_3N$), pyridine, diisopropylethylamine, lutidine, 1,8-diazobicyclo[5.4.0]undec-7-ene and 1,5-diazabicyclo[4.3.0]non-5-ene. The preferred amine base is triethylamine.

In another embodiment of the invention, the anhydride is a symmetric anhydride which contains reactive groups. Thus, the anhydride is of the formula: R—C(O)—O—C(O)—R wherein each R represents a substituted alkyl group, an alkenyl or substituted alkenyl group, an alkynyl or substituted alkynyl group, a substituted aryl group, a substituted heteroaryl group, a substituted $C_{3-8}$ cycloalkyl group or a substituted heterocyclyl group.

A preferred example is acrylic anhydride, which can be reacted with any of the auxiliaries to perform the N-acylation.

Acylation of the lactam is generally carded out by reacting the anhydride, either mixed or symmetric, with the lactam in the presence of a lithium salt and the N-containing base in a single reaction vessel. The anhydride can be formed in situ via the reaction of the requisite acid and an acyl chloride in a non-reactive solvent. Base can be included, and the reaction nm at about −20° C. After the anhydride is formed, generally over about 2 hours, the lithium salt (1.1–1.2 eq.) is added, followed by the lactam. Acylation is typically complete within 4–6 hours, after warming to room temperature.

The temperature range for the reaction is about −20° C. to about room temperature.

The acylation reaction can be conducted in any appropriate organic solvent. The preferred solvent for use herein is tetrahydrofuran.

In a preferred embodiment of the invention, a beta lactam is reacted with the anhydride to produce the N-acylated beta lactam in the presence of a nitrogen containing base, a substantially non-reactive solvent and a lithium salt.

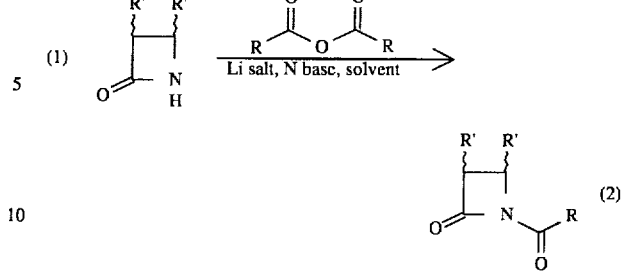

The preferred acylation reaction is carded out in the presence of lithium halide, as necessary for the acylation to occur.

The invention is further described in connection with the following non-limiting examples.

PREPARATIVE EXAMPLE 1

PREPARATION OF ACRYLIC ANHYDRIDE

To a solution of acrylic acid (1.3 equiv.) and $Et_3N$ (2.5 equiv.) in THF was added acryloyl chloride (1.2 equiv.) at −20° C. A white solid was formed. The mixture was stirred at —20° C. for 1 hr to complete the reaction, producing acrylic anhydride 1a.

PREPARATIVE EXAMPLE 2

PREPARATION OF SYMMETRIC AND ASYMMETRIC ANHYDRIDES

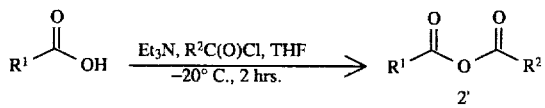

Using the procedure set forth in Preparative Example 1, anhydrides can be prepared in accordance with the following table.

TABLE 2

| Cpd | $R^1$ | $R^2$ |
|---|---|---|
| 2a | N≡C—(CH₂)₃— (pyridyl-(CH₂)₃—) | $(CH_3)_3C$— |
| 3a | t-Boc-NH—(CH₂)₄— | $(CH_3)_3C$— |
| 4a | $CH_3CH_2$— | $CH_3CH_2$— |
| 5a | H₃C-CH=CH— | H₃C-CH=CH— |
| 6a | (CH₃)₂C=CH— | (CH₃)₂C=CH— |

EXAMPLE 1

N-PROPIONYL AZETDINONE

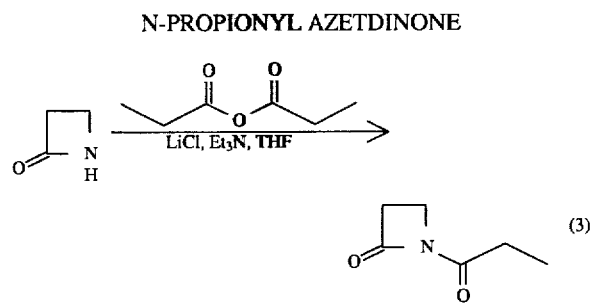

(3)

To a solution of 2-azetidinone (1.42 g, 20 mmol), lithium chloride (1.00 g, 23.5 mmol), and triethylamine (2.30 g, 23 mmol) in 100 mL of THF was added propionic anhydride (2.86 g, 22 mmol) at −20° C. The mixture was allowed to warm to 20° C. and stirred for 4 h. THF was removed under reduced pressure and the residue was partitioned between ethyl acetate (60 mL) and aqueous HCl (0.5M, 50 mL). The organic phase was then washed with HCl (0.5M, 50 mL), brine (50 mL), NaHCO$_3$ (1M, 50 mL), and brine (50 mL). The organic solution was dried over sodium sulfate and filtered. Evaporation of the solvent afforded the title compound as a colorless liquid (1.96 g).

$^1$H NMR (CDCl$_3$) d 1.15 (t, 3H), 2.70 (q, 2H), 3.05 (t, 2H), 3.60 (t, 2H).

EXAMPLE 2

PREPARATION OF N-PROPIONYL PYRROLIDINE

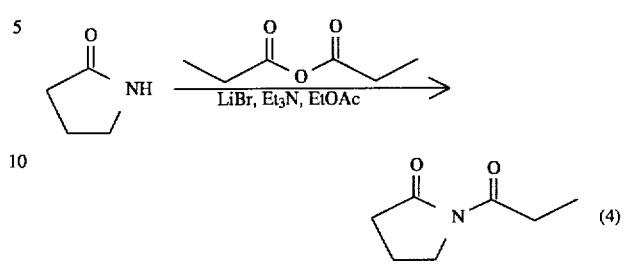

(4)

To the mixture of 2-pyrrolidine (1.70 g, 20 mmol), lithium bromide (2.13 g, 25 mmol), triethylamine (2.30 g, 23 mmol) in ethyl acetate (100 mL) was added propionic anhydride (2.86 g, 22 mmol) at −20° C. The mixture was warmed to 20° C. and stirred for 6 h. Aqueous HCl (0.5M, 50 mL) was added and the phases were separated. The organic phase was washed with HCl (0.5M, 50 mL), brine (50 mL), NaHCO$_3$ (1M, 50 mL), and brine (50 mL). The solution was dried over sodium sulfate and filtered. Evaporation of the solvent afforded the title compound as a colorless liquid (2.40 g).

$^1$H NMR (CDCL$_3$) d 1.13 (t, 3H), 2.02 (m, 2H), 2.60 (t, 2H), 2.90 (t, 2H), 3.80 (t, 2H).

EXAMPLE 3

Using the compounds set forth in Preparative Examples 1 and 2, and the procedures set forth in Examples 1 and 2, the acylating agent and lactam in columns 1 and 2 of Table 3 are reacted to produce the N-acylated product of column 3.

TABLE 3

| Acylating Agent | Lactam | Product |
| --- | --- | --- |
| 1a | | |
| 1a | | |
| 1a | | |
| 2a | | | and

TABLE 3-continued

| Acylating Agent | Lactam | Product |
|---|---|---|
| 2a | γ-butyrolactam | pyrrolidinone acylated with 4-(pyridin-4-yl)butanoyl and N-pivaloyl pyrrolidinone |
| 2a | δ-valerolactam | piperidinone acylated with 4-(pyridin-4-yl)butanoyl and N-pivaloyl piperidinone |
| 3a  t-BOC—HN(CH₂)₄—C(O)—O—C(O)—C(CH₃)₃ | β-propiolactam | β-lactam N-acylated with 5-(t-BOC-amino)pentanoyl and N-pivaloyl β-lactam |
| 3a | γ-butyrolactam | pyrrolidinone N-acylated with 5-(t-BOC-amino)pentanoyl and N-pivaloyl pyrrolidinone |
| 3a | δ-valerolactam | piperidinone N-acylated with 5-(t-BOC-amino)pentanoyl and N-pivaloyl piperidinone |

TABLE 3-continued

| Acylating Agent | Lactam | Product |
|---|---|---|
| | | and [piperidine-2,6-dione N-pivaloyl structure with C(CH₃)₃] |
| 4a  CH₃CH₂–C(O)–O–C(O)–CH₂CH₃ | β-propiolactam (4-membered, O=, NH) | N-propionyl β-propiolactam (CH₂CH₃) |
| 4a | 2-pyrrolidinone (NH) | N-propionyl-2-pyrrolidinone (CH₂CH₃) |
| 4a | 2-piperidinone (NH) | N-propionyl-2-piperidinone (CH₂CH₃) |
| 5a  CH₃–CH=CH–C(O)–O–C(O)–CH=CH–CH₃ | β-propiolactam (4-membered, NH) | N-crotonyl β-propiolactam (=CH–CH₃) |
| 5a | 2-pyrrolidinone (NH) | N-crotonyl-2-pyrrolidinone (CH₃) |
| 5a | 2-piperidinone (NH) | N-crotonyl-2-piperidinone (CH₃) |
| 6a  H₂C=C(CH₃)–C(O)–O–C(O)–C(CH₃)=CH₂ | β-propiolactam (4-membered, NH) | N-methacryloyl β-propiolactam (=CH₂, CH₃) |
| 6a | 2-pyrrolidinone (NH) | N-methacryloyl-2-pyrrolidinone (=CH₂, CH₃) |
| 6a | 2-piperidinone (NH) | N-methacryloyl-2-piperidinone (=CH₂, CH₃) |

What is claimed is:

1. A process of synthesizing an N-acyl auxiliary compound of the formula:

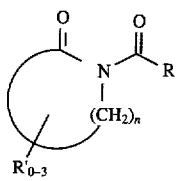
(A)

wherein:

R and R' independently represent members selected from the group consisting of:

(a) —$C_{1-6}$ alkyl, —$C_{2-6}$ alkenyl or —$C_{2-6}$ alkynyl;

(b) —$C_{1-6}$ alkyl, —$C_{2-6}$ alkenyl or —$C_{2-6}$ alkynyl substituted with from 1-3 groups selected from: —$NH_2$; —OH; —COOH, —COO($C_{1-4}$) alkyl, —$OC_{1-4}$ alkyl; —C(O)—$C_{1-4}$ alkyl; —OC(O)$C_{1-4}$ alkyl; —NH($C_{1-6}$ alkyl); —NH($C_{2-6}$ alkenyl); —NH($C_{2-6}$ alkynyl); —N($C_{1-6}$ alkyl)$_2$; —N($C_{2-6}$ alkenyl)$_2$; —N($C_{2-6}$ alkynyl)$_2$; —OC(O)$NH_2$; —OC(O)NH$C_{1-4}$ alkyl; —OC(O)N($C_{1-4}$ alkyl)$_2$; -aryl; -heteroaryl; —$C_{3-8}$ cycloalkyl; -heterocyclyl; -halo; —NHC(O)O$C_{1-6}$ alkyl; —N($C_{1-4}$ alkyl)C(O)O$C_{1-6}$ alkyl, and -aryl, heteroaryl, $C_{3-8}$ cycloalkyl or heterocyclyl substituted with from 1-3 groups selected from halo, hydroxy, —$C_{1-4}$ alkyl, —$C_{1-4}$ alkoxy, hydroxy-$C_{1-4}$ alkyl, -amino, —NH($C_{1-4}$ alkyl) and —N($C_{1-4}$ alkyl)$_2$;

(c) aryl, heteroaryl, $C_{3-8}$ cycloalkyl or heterocyclyl, unsubstituted or substituted with from 1-3 groups selected from halo, hydroxy, $C_{1-4}$ alkoxy, hydroxy-$C_{1-4}$ alkyl, amino, $C_{1-4}$ alkylamino, and di-$C_{1-4}$ alkylamino;

(d) $C_{1-6}$ alkyl, $C_{2-6}$ alkenyl or $C_{2-6}$ alkynyl substituted with (1) 1 to 3 groups selected from: —NHP; —$NP_2$; —OP; —$CO_2$P; —NP($C_{1-6}$ alkyl); —NP($C_{2-6}$ alkenyl); —NP($C_{2-6}$ alkynyl); —OC(O)NHP; —OC(O)$NP_2$; OC(O)NP($C_{1-6}$ alkyl); —NPC(O)O($C_{1-6}$ alkyl); aryl, heteroaryl, $C_{3-8}$ cycloalkyl or heterocyclyl substituted with from 1-3 groups selected from —OP, —$C_{1-3}$ alkyl-OP, —NHP, —$NP_2$, —$C_{1-3}$ alkyl-NHP, —$C_{1-3}$ alkyl-$NP_2$, —NP—$C_{1-3}$ alkyl, and 0-3 members selected from the group consisting of: halo, $C_{1-3}$ alkyl, $C_{1-3}$ alkoxy, and —N($C_{1-3}$ alkyl)$_2$;
and (2) 0 to 3 groups selected from the group consisting of: —COO($C_{1-3}$) alkyl, —$OC_{1-4}$ alkyl; —C(O)—$C_{1-4}$ alkyl; —N($C_{1-6}$ alkyl)$_2$; —N($C_{2-6}$ alkenyl)$_2$; —N($C_{2-6}$ alkynyl)$_2$; —OC(O)N($C_{1-4}$ alkyl)$_2$; aryl; heteroaryl; $C_{3-8}$ cycloalkyl; heterocyclyl; halo; —N($C_{1-3}$ alkyl)C(O)O$C_{1-6}$ alkyl; and aryl, heteroaryl, —$C_{3-8}$ cycloalkyl or heterocyclyl substituted with from 1-3 groups selected from: halo, —$C_{1-3}$ alkyl, —$C_{1-3}$ alkoxy and —N($C_{1-3}$ alkyl)$_2$, and (e) aryl, heteroaryl, $C_{3-8}$ cycloalkyl or heterocyclyl substituted with:

(1) from 1 to 3 members selected from the group consisting of: —OP, —$C_{1-4}$ alkyl-OP, —NHP, —$NP_2$, —$C_{1-4}$ alkyl-NHP, —$C_{1-4}$ alkyl-$NP_2$ and —NP$C_{1-4}$ alkyl,
and (2) from 0 to 3 members selected from the group consisting of: halo, —$C_{1-4}$ alkoxy and —N($C_{1-4}$ alkyl)$_2$;

wherein P represents a protecting group, and n represents an integer of from 2 through 7, comprising reacting a compound of the formula:

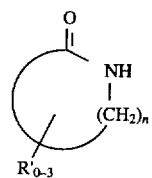
(B)

wherein n and R' are as previously defined, with an anhydride represented by the formula:

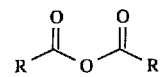
(C)

wherein the R groups are the same or different, and are as previously defined, in the presence of a lithium salt and an amine base to produce:

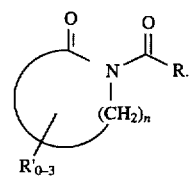
(A)

2. A process in accordance with claim 1 wherein a compound of the formula

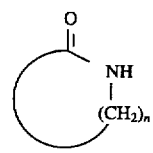
(B')

is reacted with an anhydride represented by the formula:

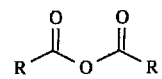
(C)

wherein R and n are as previously defined, in the presence of a lithium salt and an amine base to produce:

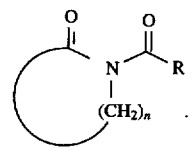
(A')

3. A process in accordance with claim 2 wherein the compound:

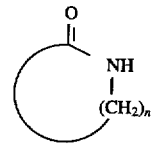
(B')

is a member selected from the group consisting of:

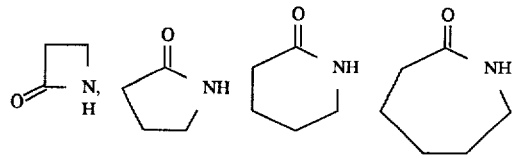

-continued
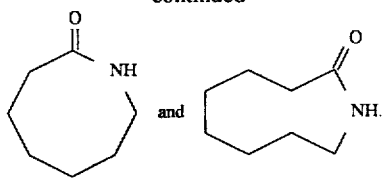
4. A process in accordance with claim 1 wherein the lithium salt is selected from the group consisting of: lithium bromide, lithium chloride, lithium fluoride, lithium iodide, lithium perchlorate, lithium nitrate, lithium sulfate and lithium tetrafluoroborate.
* * * * *